(12) United States Patent
Jacene et al.

(10) Patent No.: US 9,381,263 B2
(45) Date of Patent: Jul. 5, 2016

(54) FLASH STERILIZATION CONTAINER

(71) Applicant: Specialty Surgical Instrumentation Inc., Antioch, TN (US)

(72) Inventors: Michael Jacene, Douglas, MA (US); Jerry R. Griffiths, Norwell, MA (US); Christopher M. Johnson, Abington, MA (US); Ali Kiapour, Providence, RI (US)

(73) Assignee: Specialty Surgical Instrumentation Inc., Antioch, TN (US)

(*) Notice: Subject to any disclaimer, the term of this patent is extended or adjusted under 35 U.S.C. 154(b) by 47 days.

(21) Appl. No.: 13/970,752

(22) Filed: Aug. 20, 2013

(65) Prior Publication Data
US 2014/0056759 A1 Feb. 27, 2014

Related U.S. Application Data

(60) Provisional application No. 61/692,807, filed on Aug. 24, 2012.

(51) Int. Cl.
*A61L 2/07* (2006.01)
*F16K 17/04* (2006.01)
*A61L 2/26* (2006.01)

(52) U.S. Cl.
CPC ... *A61L 2/07* (2013.01); *A61L 2/26* (2013.01); *F16K 17/0493* (2013.01); *A61L 2202/121* (2013.01); *A61L 2202/122* (2013.01)

(58) Field of Classification Search
CPC ................. A61L 2/07; A61L 2/26; B01J 3/04
USPC ............................................................ 422/26
See application file for complete search history.

(56) References Cited

U.S. PATENT DOCUMENTS

| | | | | |
|---|---|---|---|---|
| 3,949,934 | A * | 4/1976 | Goglio | 383/103 |
| 4,748,003 | A | 5/1988 | Riley | |
| 5,097,865 | A * | 3/1992 | Riley | 137/529 |
| 5,240,605 | A | 8/1993 | Winzeler | |
| 6,468,482 | B1 | 10/2002 | Frieze et al. | |
| 6,589,477 | B1 | 7/2003 | Frieze et al. | |
| 2002/0136679 | A1 | 9/2002 | Frieze et al. | |
| 2003/0118491 | A1 | 6/2003 | Frieze et al. | |
| 2004/0011689 | A1 | 1/2004 | Bauer | |
| 2004/0222116 | A1 | 11/2004 | Bauer | |
| 2012/0156096 | A1* | 6/2012 | Allen et al. | 422/38 |

FOREIGN PATENT DOCUMENTS

EP     2366410 A1 *  9/2011

OTHER PUBLICATIONS

EPO Search Report, EPO, Nov. 14, 2013.

* cited by examiner

*Primary Examiner* — Kevin Joyner
*Assistant Examiner* — Holly Mull
(74) *Attorney, Agent, or Firm* — Hayes Soloway, P.C.

(57) ABSTRACT

A flash sterilization container includes a hermetically sealed rigid and impermeable metal bellow valve. Upon pressurization of the external environment with steam the height of the bellow valve is reduced and this opens the valve thereby allowing steam to enter the sterilization container. Reducing the pressure outside of the sterilization container to atmospheric pressure increases the height of the bellow valve and closes the valve, thereby isolating the sterilized objects within the sterilization container.

22 Claims, 12 Drawing Sheets ial application Ser. No. 61/692,807 filed on Aug. 24, 2012 and entitled FLASH STERILIZATION CONTAINER which is commonly assigned and the contents of which are expressly incorporated herein by reference.

FLASH STERILIZATION CONTAINER

CROSS REFERENCE TO RELATED CO-PENDING APPLICATIONS

This application claims the benefit of U.S. provisional application Ser. No. 61/692,807 filed on Aug. 24, 2012 and entitled FLASH STERILIZATION CONTAINER which is commonly assigned and the contents of which are expressly incorporated herein by reference.

FIELD OF THE INVENTION

The present invention relates to a flash sterilization container, and more particularly to a flash sterilization container with a hermetically sealed metal bellow valve.

BACKGROUND OF THE INVENTION

Medical devices and instruments need to be sterilized prior to being used in surgical procedures. Sterilization reduces the risk of infection from microbes that may be present on the medical devices and instruments. One of the most commonly used sterilization techniques involves placing the objects that need to be sterilized in a container and then heating the container with the enclosed objects to a temperature and for a time sufficient to kill any present microbes.

Flash sterilization refers to using steam to sterilize the objects in the sterilization container. During flash sterilization unwrapped medical devices and instruments are exposed to steam for a certain time and then are used in surgical procedures.

A typical flash sterilization container includes an open base portion, a tray and a lid portion. The objects to be sterilized are placed in the tray, and then the tray is placed in the base portion. Next, the lid is placed on top of the base portion opening and is secured to the base portion. A vent is usually incorporated either on the lid portion and/or the base portion. The vent allows pumping out and injecting gasses into the closed container. The vent usually also includes a filter that prevents microbes from exiting the closed container.

The vent usually includes an aperture formed in the vent carrying component and a valve placed in the aperture. The valve is usually a mechanical valve that includes elastomeric sealing materials. The elastomeric sealing materials have the tendency of developing leaks after several sterilization cycles. Furthermore, the prior art valves include several mechanical components that need to be precisely dimensioned in order to provide a good seal. Furthermore, the reaction time for opening and closing these mechanical valves is usually long for today's flash sterilization purposes. Accordingly, an improved valve mechanism is desirable for providing fast flash sterilization of medical devices and instruments.

SUMMARY OF THE INVENTION

The present invention provides a flash sterilization container that includes a hermetically sealed rigid and impermeable metal bellow valve. The valve is designed for use in an autoclave environment. Upon pressurization of the external environment with steam the height of the bellow valve is reduced and this opens the valve and allows steam to enter the sterilization container. Reducing the pressure outside of the sterilization container to atmospheric pressure increases the height of the bellow valve and this closes the valve and isolates the sterilized objects within the sterilization container.

In general, in one aspect, the invention features a sterilization container comprising a container and a lid. The container includes a base, four side walls and an open top. The lid is shaped and dimensioned to cover and seal the entire open top of the container. The lid comprises an aperture that is sealed with a pressure actuated valve assembly. The pressure actuated valve assembly includes a cylindrical metal component and a hermetically sealed metal bellow component positioned within the cylindrical metal component. The pressure actuated valve assembly opens or closes by decreasing or increasing the height of the hermetically sealed metal bellow component, respectively.

Implementations of this aspect of the invention may include one or more of the following features. The hermetically sealed metal bellow component has a hollow metal bellow body comprising a hermetically sealed inner space that contains a small amount of air. The hollow metal bellow body has a dome-shaped closed bottom and an open top, and a plate is welded to the open top of the hollow metal bellow body, thereby sealing hermetically the inner space of the hollow metal bellow body and trapping the small amount of air within the hermetically sealed inner space. Upon increasing the pressure outside of the sterilization container with steam the height of the hermetically sealed metal bellow decreases and causes the pressure actuated valve assembly to close and to allow steam to enter the sterilization container. Upon reducing the pressure outside of the sterilization container to atmospheric pressure, the height of the hermetically sealed metal bellow increases and causes the pressure actuated valve assembly to open, and thereby to isolate sterilized objects within the sterilization container. The lid is secured to the container top with clamps or via a snap-fit mechanism. The lid further includes a rubber relief valve. The lid further includes a perforated metal plate against which the pressure actuated valve assembly seals. The cylindrical metal component has a cylindrical body having an outward extending top ring, an inward extending bottom ring and a through aperture. The top ring includes openings dimensioned to receive bolts for securing the pressure actuated valve assembly to the lid and wherein the bottom ring is dimensioned to receive the dome-shaped closed bottom of the hermetically sealed metal bellow component. The sterilization container further includes a tray supported within the container and the tray is perforated or meshed and is shaped and dimensioned to support objects that need to be sterilized. The cylindrical metal component and the hermetically sealed metal below component comprise rigid and impermeable metals. The base may also include an aperture that is sealed with a pressure actuated valve assembly.

In general, in another aspect, the invention features a sterilization method including providing a container comprising a base, four side walls and an open top and placing objects to be sterilized within the container. Next, providing a lid shaped and dimensioned to cover and seal the entire open top of the container and sealing the container. The lid comprises an aperture that is sealed with a pressure actuated valve assembly. The pressure actuated valve assembly includes a cylindrical metal component and a hermetically sealed metal bellow component positioned within the cylindrical metal component. The pressure actuated valve assembly opens or closes by decreasing or increasing the height of the hermetically sealed metal bellow component, respectively.

Among the advantages of this invention may be one or more of the following. The all metal bellow valve is capable of withstanding multiple sterilization cycles without exhibiting any leakage. The reaction time of the metal bellow valve is significantly reduced compared to the prior art valves, thus replicating the true response time of the autoclave environment. In case of valve failure, the valve remains in the closed position and thus the sterilization container remains closed and the sterilized objects are not affected. Furthermore, due to the reduced number of components, the reliability of the valve is increased and the manufacturing complexity is reduced.

The details of one or more embodiments of the invention are set forth in the accompanying drawings and description bellow. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views.

DETAILED DESCRIPTION OF THE INVENTION

Figure 1:
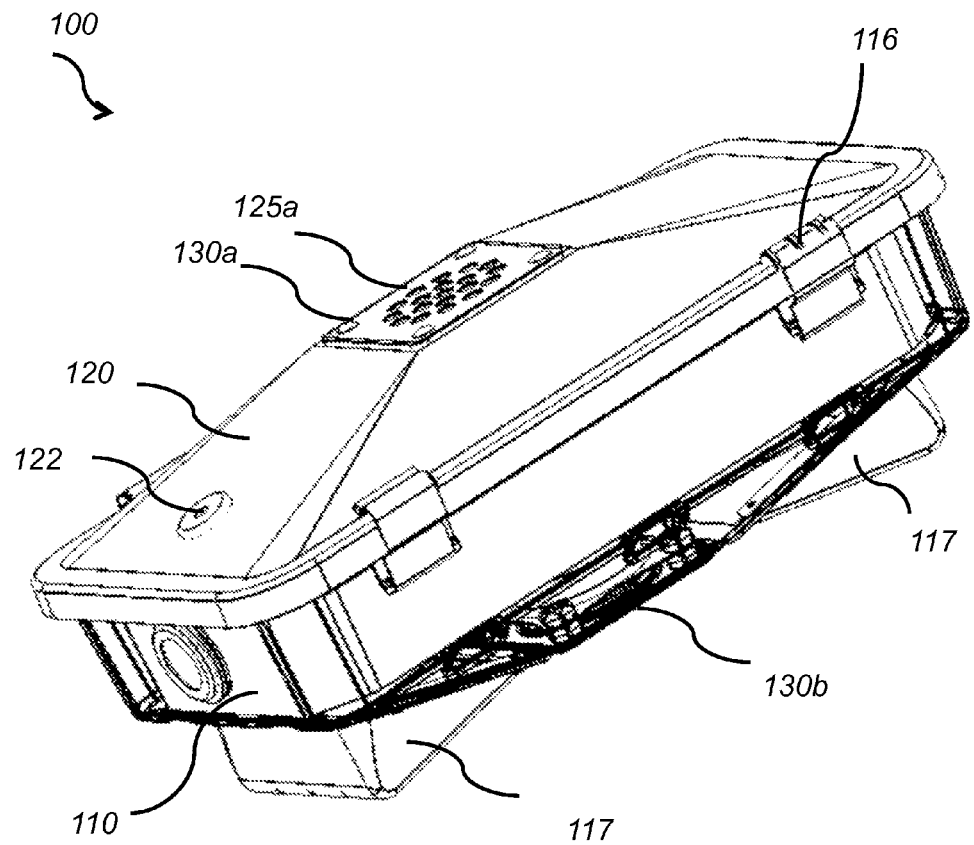
FIG. 1 is a top perspective view of a sterilization container according to this invention.
Figure 2:
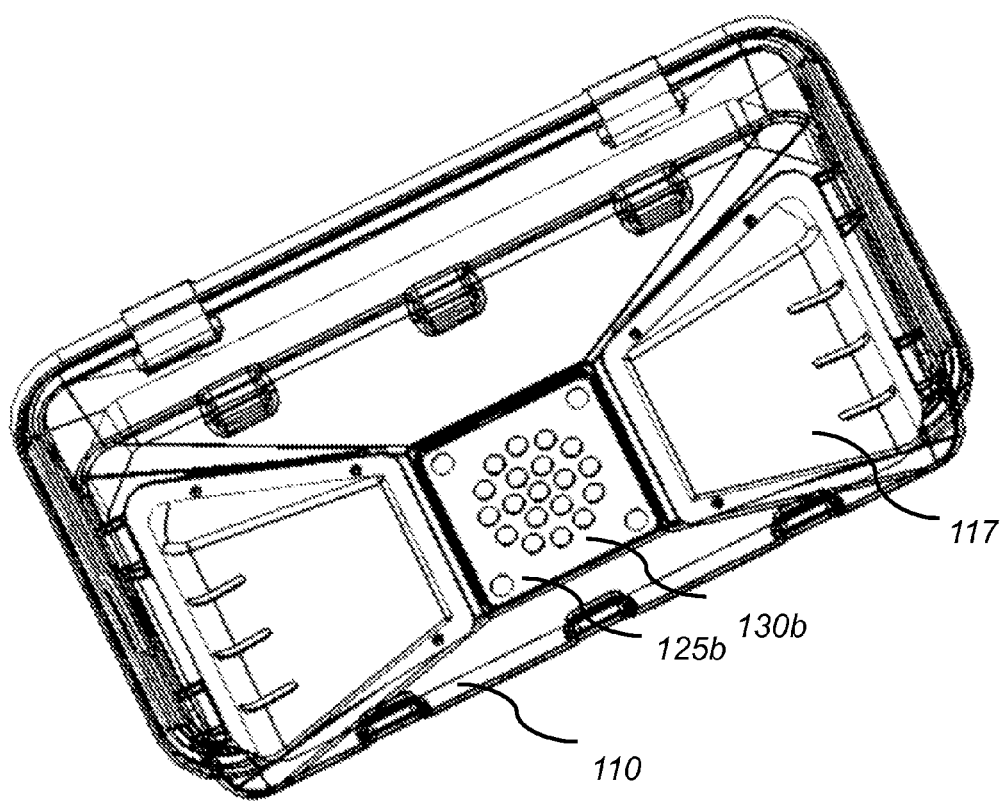
FIG. 2 is a bottom perspective view of the sterilization container of FIG. 1.

Referring to FIG. 1, FIG. 2, FIG. 3A, FIG. 3B and FIG. 3C, sterilization container 100 includes a base 110 and a lid 120. Lid 120 is removably sealed to the base 110. A perforated or mesh tray 140 is supported within the base 110 and holds medical devices, instruments and any other object that needs to be sterilized. Lid 120 is secured to the base 110 with clamps 116 or via a snap-fit mechanism. In this embodiment both the lid 120 and the base 110 include top and bottom apertures that are sealed with pressure-actuated valve assemblies 130a, 130b, respectively. Lid 120 also includes a rubber relief valve 125 and a perforated metal plate 125a against which the valve 130a seals. Base also includes a perforated metal plate 125b against which the valve 130b seals and feet 117.

Figure 3A:
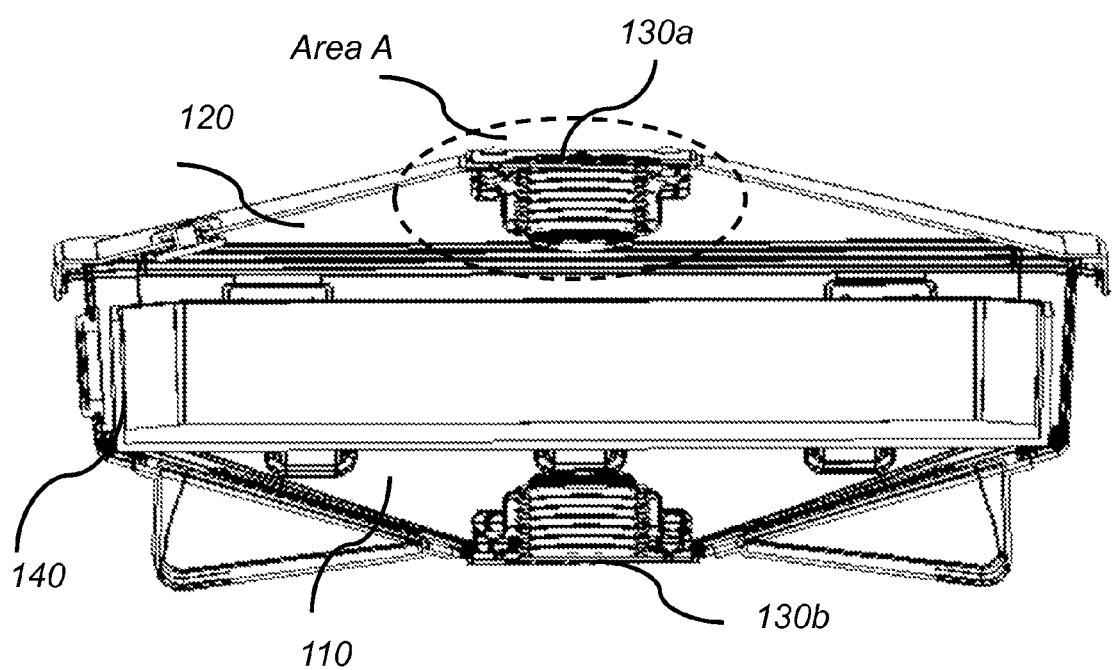
FIG. 3A is side cross-sectional view of the sterilization container of FIG. 1.
Figure 3B:
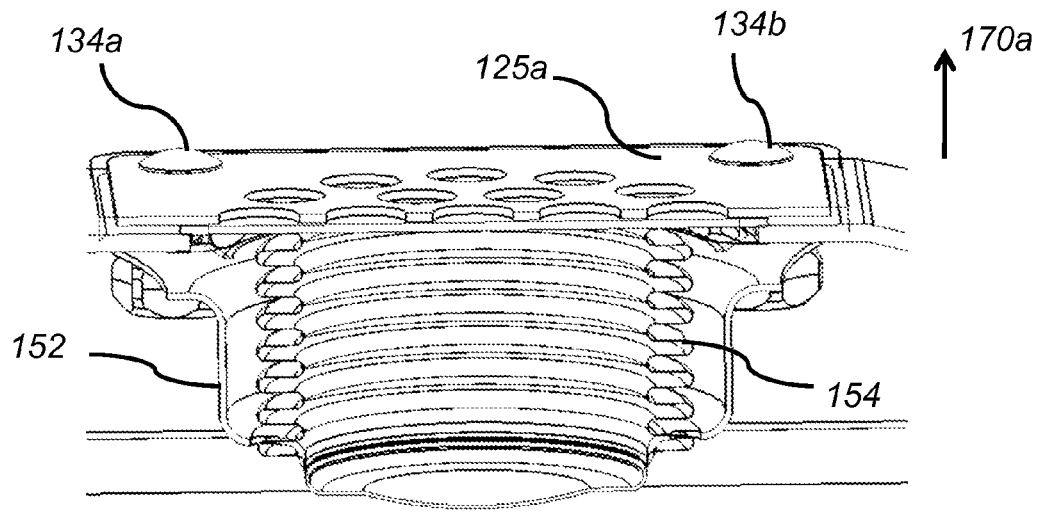
FIG. 3B is a detailed view of area A in FIG. 3A with the valve in the closed position.
Figure 3C:
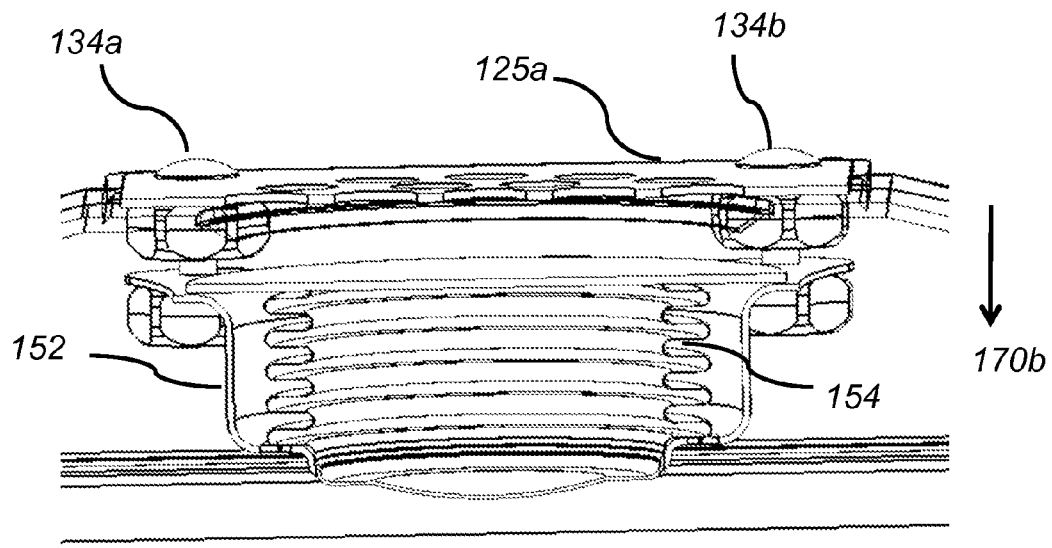
FIG. 3C is a detailed view of area A in FIG. 3A with the valve in the open position.
Figure 4:
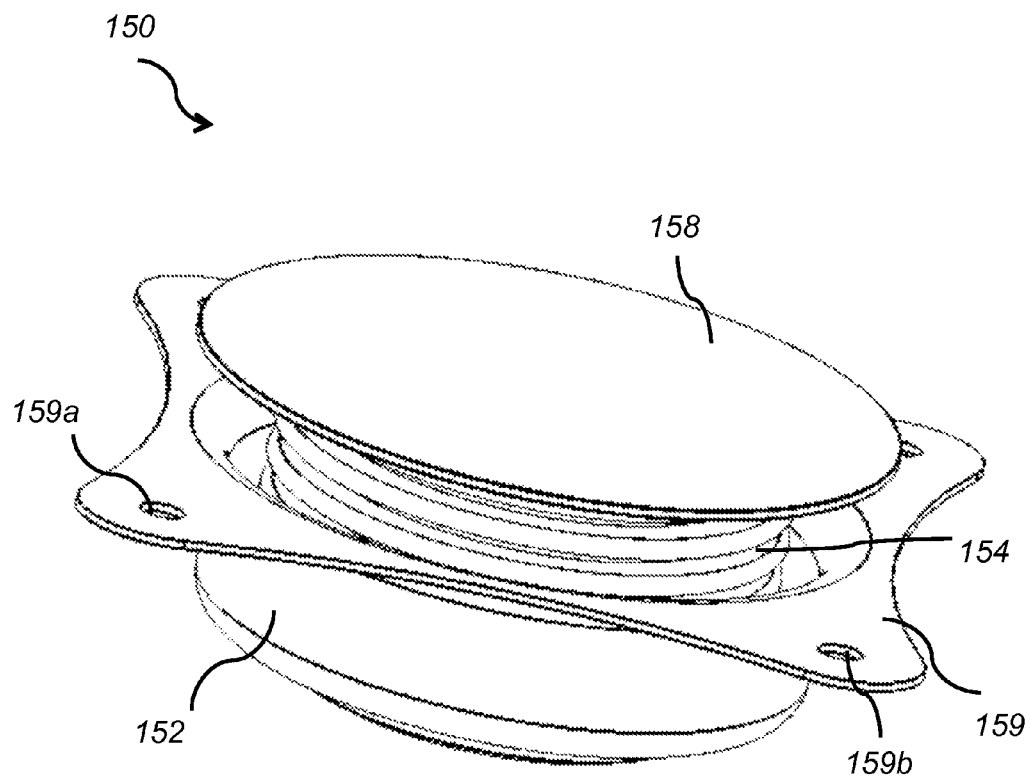
FIG. 4 is a top perspective view of a metal bellow valve of this invention.
Figure 5:
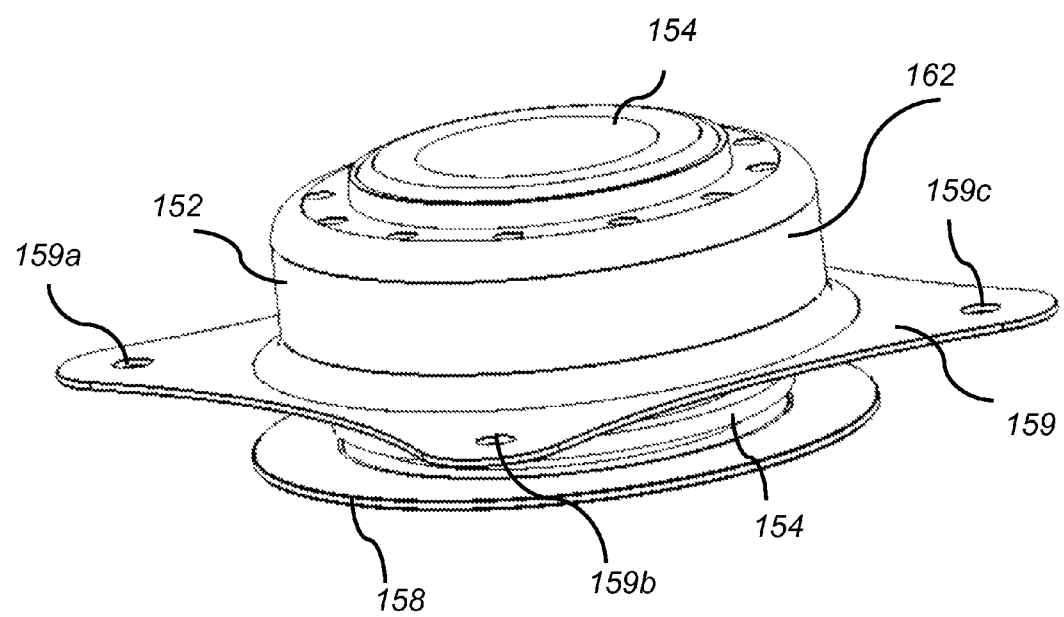
FIG. 5 is a bottom perspective view of the metal bellow valve of FIG. 4.
Figure 6:
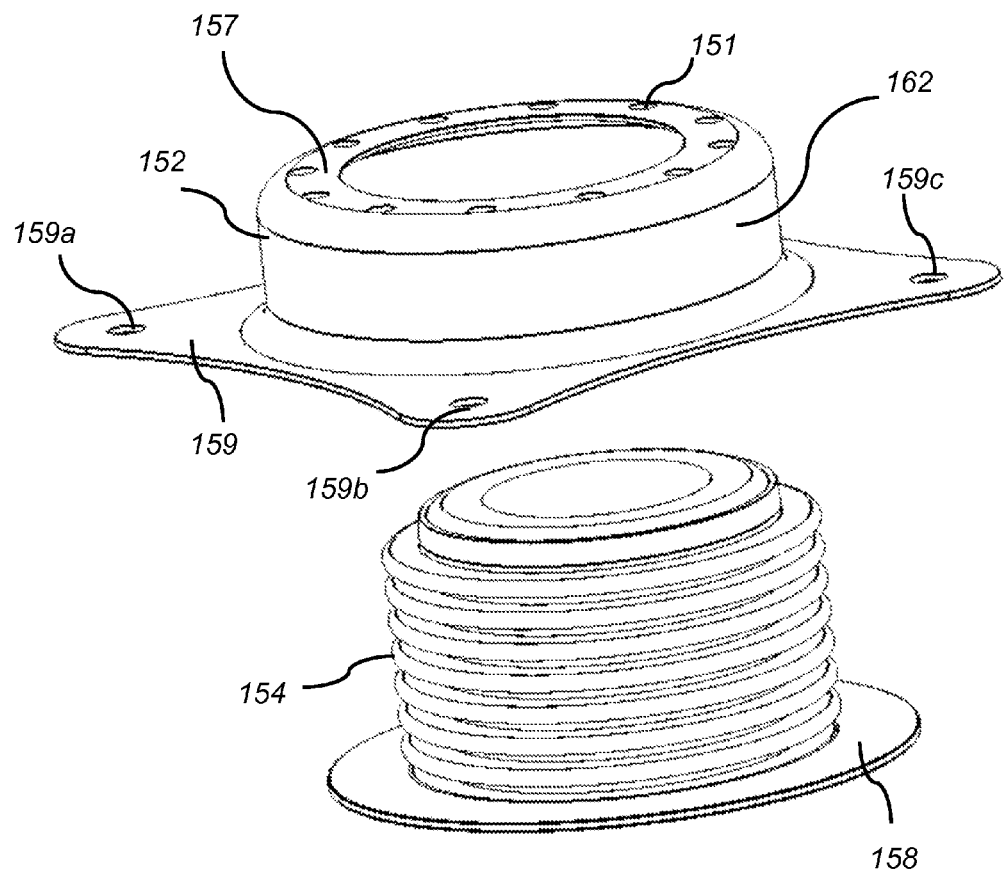
FIG. 6 is an exploded bottom perspective view of the valve of FIG. 5.
Figure 7:
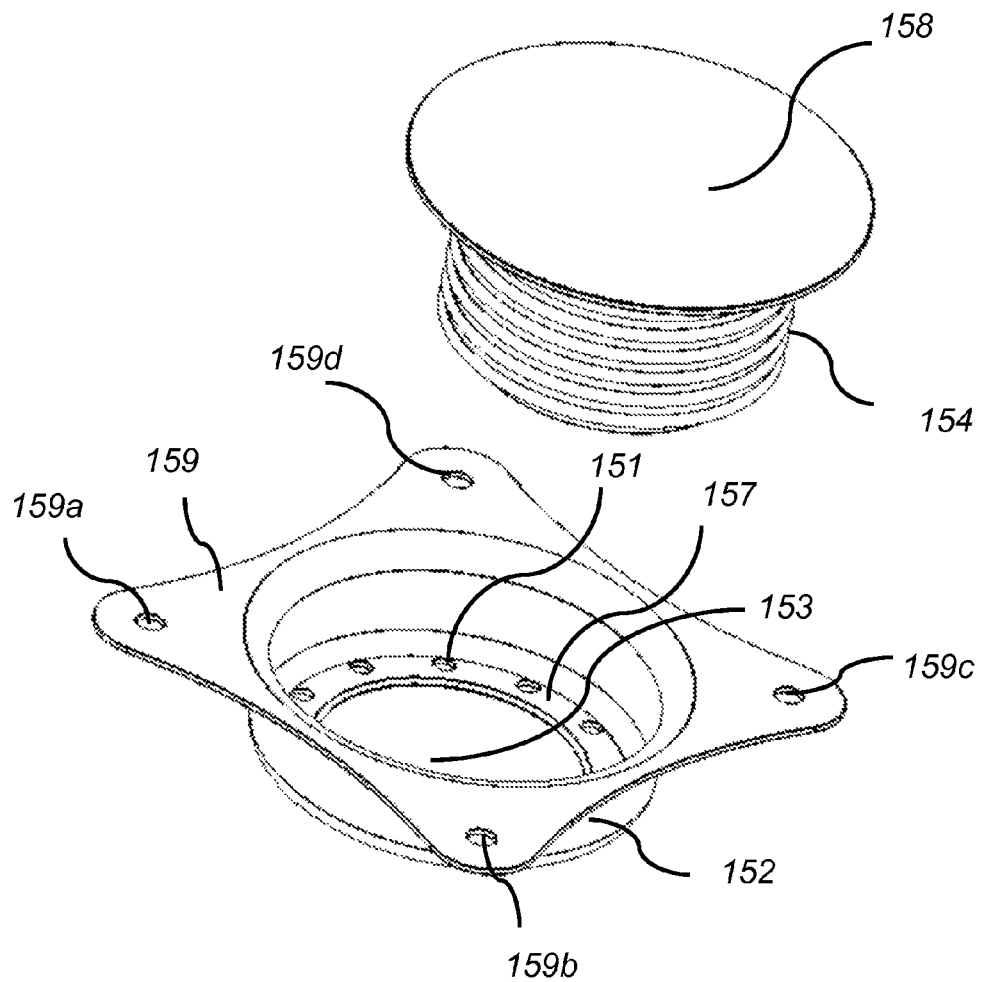
FIG. 7 is an exploded top perspective view of the valve of FIG. 5.
Figure 8:
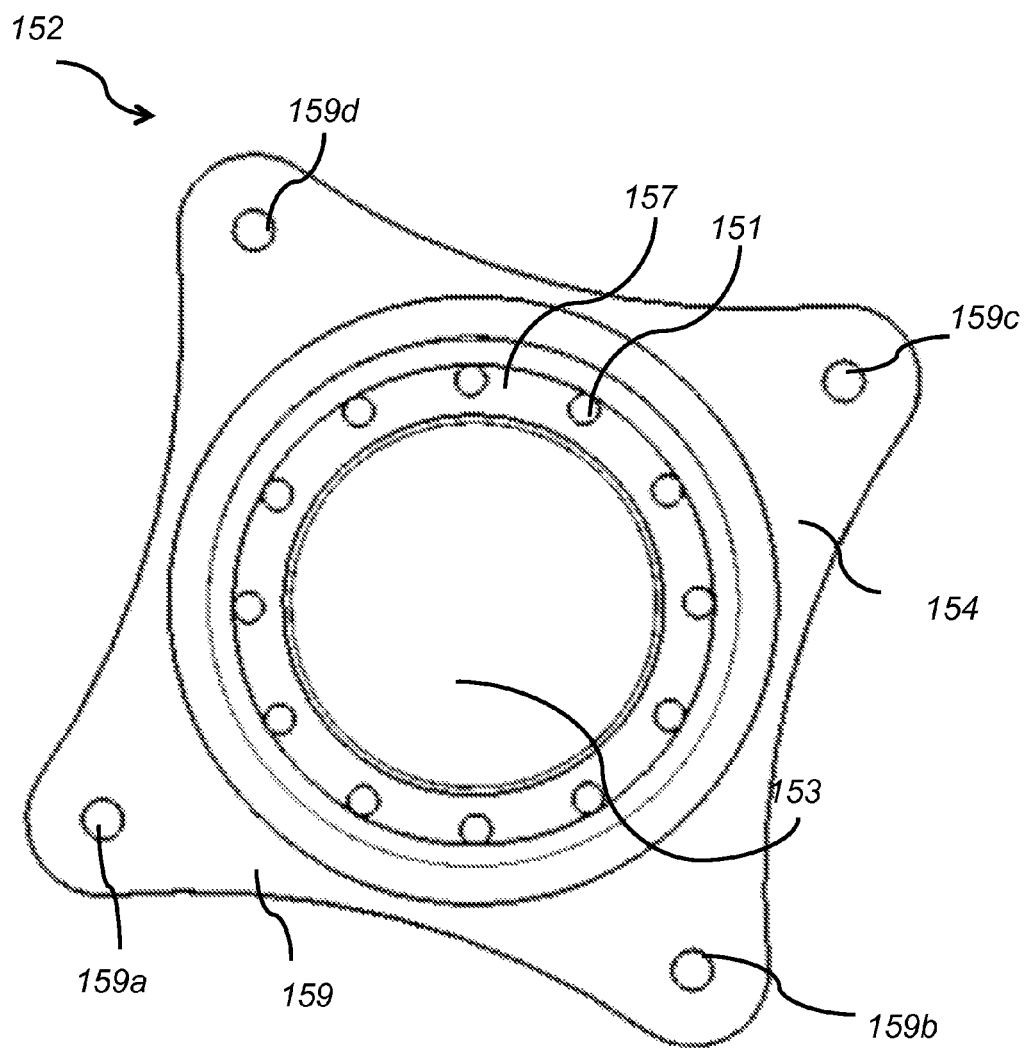
FIG. 8 is a top view of the cylindrical metal component of the valve of FIG. 5.
Figure 9:
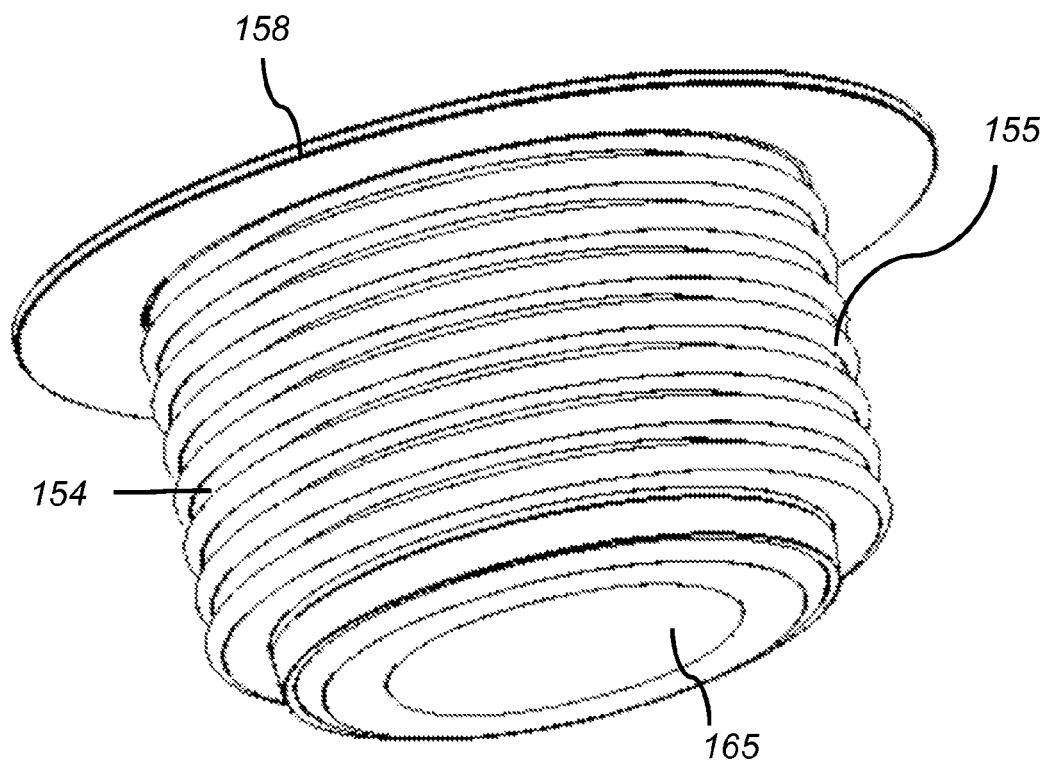
FIG. 9 is a side perspective view of the metal bellow component of the valve of FIG. 5.
Figure 10:
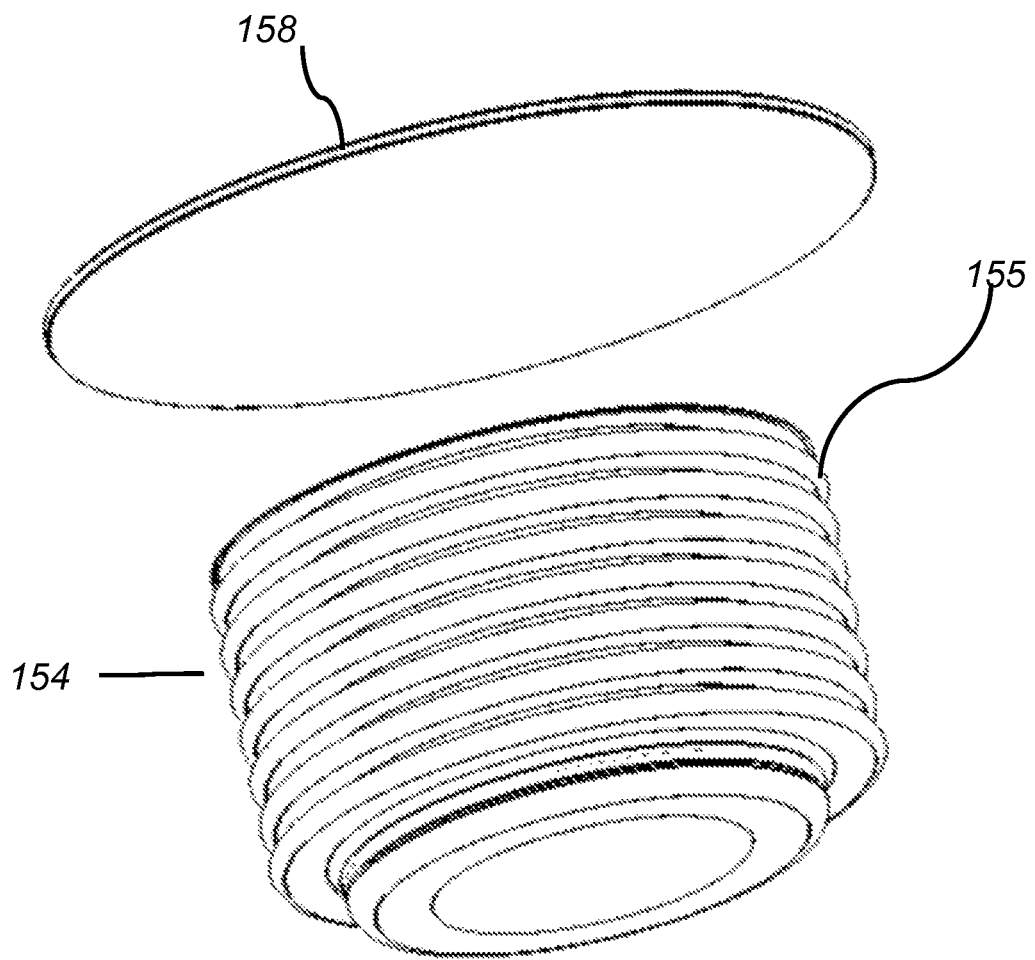
FIG. 10 is an exploded side perspective view of the metal bellow component of the valve of FIG. 5.
Figure 11:
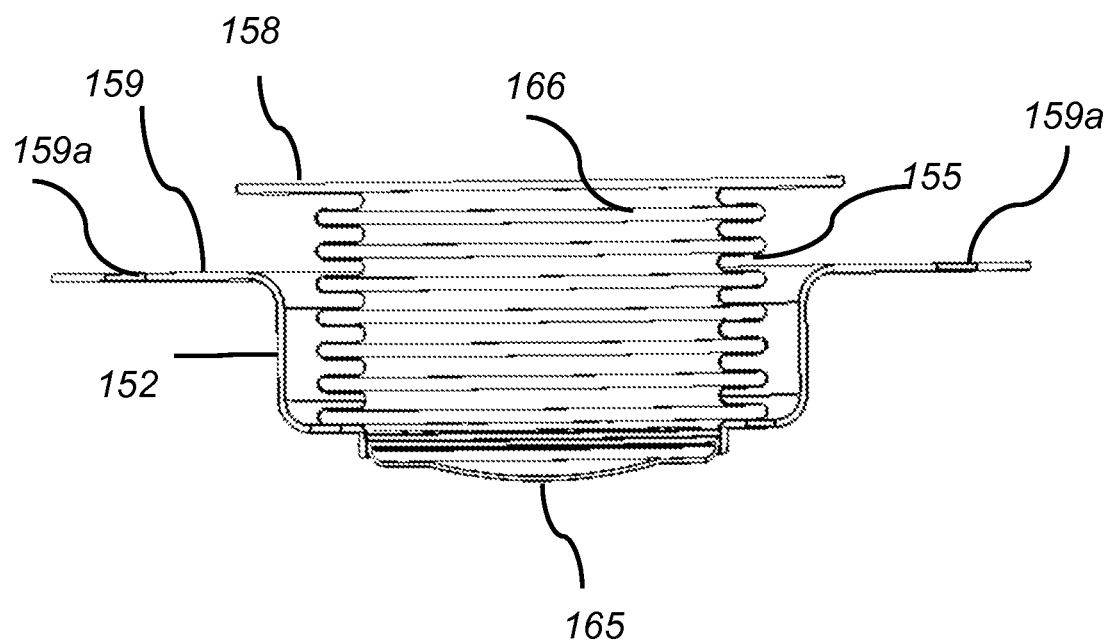
FIG. 11 is a cross-section side view of the side perspective view of the valve of FIG. 5.

Referring to FIG. 3B, FIG. 3C, and FIG. 4-FIG. 11, each of the valve assemblies 130a, 130b includes a movable metal bellow component 154 and a cylindrical metal component 152. Cylindrical component 152 includes a cylindrical body 162 having an outward extending top ring 159, an inward extending bottom ring 157 and a through aperture 153. The top ring 159 includes openings 159a, 159b, 159c and 159d configured to receive bolts 134 for securing the valve assembly to the lid 120 or the base 110. The bottom ring 157 includes openings 151 and is dimensioned to receive and come in contact with the bottom portion of the bellow component 154. The bellow component 154 includes a hollow metal bellow body 155, a dome-shaped closed bottom 165, and a top plate 158. The top plate 158 is welded onto the top edge of the metal bellow body 155, thereby sealing hermetically the inner space 166 of the bellow body and trapping a small amount of air in the bellow inner space 166. Upon pressurization of the external environment with steam the height of the bellow body 155 is reduced along the indicated direction 170b and this opens the valve thereby allowing steam to enter the sterilization container 100, as shown in FIG. 3C. In one example, the sterilization temperature is 270° F. and with the valve in the open position, steam is injected in the container 100 and the objects that are held within the container are sterilized. Reducing the pressure outside of the sterilization container to atmospheric pressure increases the height of the bellow body 155 along 170a, thereby bringing the top plate 158 of the bellow body 155 in contact with the top perforated plate 157 of the lid 120, as shown in FIG. 3B. This height increase of the bellow body 155 closes the valve, and thereby isolates the sterilized objects within the sterilization container. Bellow component 154 and cylindrical metal component 152 are made of rigid and impermeable material such as stainless steel, or any other metal capable of withstanding the sterilization temperatures.

Several embodiments of the present invention have been described. Nevertheless, it will be understood that various modifications may be made without departing from the spirit and scope of the invention. Accordingly, other embodiments are within the scope of the following claims.

What is claimed is:

1. A sterilization container comprising:
a container comprising a base, four side walls and an open top;
a lid shaped and dimensioned to cover and seal the entire open top of the container;
wherein the lid comprises an aperture that is sealed with a pressure actuated valve assembly;
wherein the pressure actuated valve assembly comprises a cylindrical metal component and a hermetically sealed metal bellow component positioned within the cylindrical metal component; and
wherein the pressure actuate valve assembly opens or closes by decreasing or increasing the height of the hermetically sealed metal bellow component, respectively; and
wherein the hermetically sealed metal bellow component comprises a hollow metal bellow body and a dome-shaped closed bottom; and
wherein the cylindrical metal component comprises an elongated cylindrical body having an outward extending top ring, an inward extending bottom ring and a through aperture, and wherein the top ring comprises openings dimensioned to receive bolts for securing the pressure actuated valve assembly to the lid and wherein the bottom ring is shaped and dimensioned to receive the dome-shaped closed bottom of the hermetically sealed metal bellow component.

2. The sterilization container of claim 1, wherein the hollow metal bellow body comprises a hermetically sealed inner space comprising a small amount of air.

3. The sterilization container of claim 2, wherein the hollow metal bellow body comprises an open top, and wherein a plate is welded to the open top of the hollow metal bellow body, thereby sealing hermetically the inner space of the hollow metal bellow body and trapping the small amount of air within the hermetically sealed inner space.

4. The sterilization container of claim 1, wherein upon increasing the pressure outside of the sterilization container with steam the height of the hermetically sealed metal bellow decreases and causes the pressure actuated valve assembly to open and to allow steam to enter the sterilization container; and wherein upon reducing the pressure outside of the sterilization container to atmospheric pressure, the height of the hermetically sealed metal bellow increases and causes the pressure actuated valve assembly to close, and thereby to isolate sterilized objects within the sterilization container.

5. The sterilization container of claim 1, wherein the lid is secured to the container top with clamps or via a snap-fit mechanism.

6. The sterilization container of claim 1, wherein the lid further includes a rubber relief valve.

7. The sterilization container of claim 1, wherein the lid further includes a perforated metal plate against which the pressure actuated valve assembly seals.

8. The sterilization container of claim 1, further comprising a tray supported within the container and wherein the tray is perforated or meshed and is shaped and dimensioned to support objects that need to be sterilized.

9. The sterilization container of claim 1, wherein the cylindrical metal component and the hermetically sealed metal below component comprise rigid and impermeable metals.

10. The sterilization container of claim 1 wherein the base comprises an aperture that is sealed with a pressure actuated valve assembly.

11. The sterilization method of claim 1, wherein the valve assembly is an all-metal valve assembly.

12. A sterilization method comprising: providing a container comprising a base, four side walls and an open top and placing objects to be sterilized within the container; providing a lid shaped and dimensioned to cover and seal the entire open top of the container; wherein the lid comprises an aperture that is sealed with a pressure actuated valve assembly; wherein the pressure actuated valve assembly comprises a cylindrical metal component and a hermetically sealed metal bellow component positioned within the cylindrical metal component; and wherein the pressure actuated valve assembly opens or closes by decreasing or increasing the height of the hermetically sealed metal bellow component, respectively; and
  wherein the pressure actuate valve assembly opens or closes by decreasing or increasing the height of the hermetically sealed metal bellow component, respectively; and
  wherein the hermetically sealed metal bellow component comprises a hollow metal bellow body and a dome-shaped closed bottom; and
  wherein the cylindrical metal component comprises an elongated cylindrical body having an outward extending top ring, an inward extending bottom ring and a through aperture, and wherein the top ring comprises openings dimensioned to receive bolts for securing the pressure actuated valve assembly to the lid and wherein the bottom ring is shaped and dimensioned to receive the dome-shaped closed bottom of the hermetically sealed metal bellow component.

13. The sterilization method of claim 12, wherein the hollow metal bellow body comprises a hermetically sealed inner space comprising a small amount of air.

14. The sterilization method of claim 13, wherein the hollow metal bellow body comprises an open top, and wherein a plate is welded to the open top of the hollow metal bellow body, thereby sealing hermetically the inner space of the hollow metal bellow body and trapping the small amount of air within the hermetically sealed inner space.

15. The sterilization method of claim 12, wherein upon increasing the pressure outside of the sterilization container with steam the height of the hermetically sealed metal bellow is decreased and causes the pressure actuated valve assembly to open and to allow steam to enter the sterilization container; and wherein upon reducing the pressure outside of the sterilization container to atmospheric pressure, the height of the hermetically sealed metal bellow increases and causes the pressure actuated valve assembly to close, and thereby to isolate sterilized objects within the sterilization container.

16. The sterilization method of claim 12, wherein the lid is secured to the container top with clamps or via a snap-fit mechanism.

17. The sterilization method of claim 12, wherein the lid further includes a rubber relief valve.

18. The sterilization method of claim 12, wherein the lid further includes a perforated metal plate against which the pressure actuated valve assembly seals.

19. The sterilization method of claim 12, further comprising providing a tray that is supported within the container and wherein the tray is perforated or meshed and is shaped and dimensioned to support the objects to be sterilized.

20. The sterilization method of claim 12, wherein the cylindrical metal component and the hermetically sealed metal below component comprise rigid and impermeable metals.

21. The sterilization container of claim 12, wherein the base comprises an aperture that is sealed with a pressure actuated valve assembly.

22. The sterilization method of claim 12, wherein the valve assembly is an all-metal valve assembly.

* * * * *